(12) United States Patent
Kumaraswamy et al.

(10) Patent No.: US 6,199,437 B1
(45) Date of Patent: Mar. 13, 2001

(54) APPARATUS FOR STUDYING THE EFFECTS OF FLOW FIELDS IMPOSED ON A MATERIAL DURING PROCESSING

(75) Inventors: Guruswamy Kumaraswamy; Ravi K. Verma; Julia A. Kornfield, all of Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/267,181

(22) Filed: Mar. 12, 1999

Related U.S. Application Data
(60) Provisional application No. 60/077,947, filed on Mar. 13, 1998.

(51) Int. Cl.$^7$ .................................................. G01N 11/08
(52) U.S. Cl. .......................................................... 73/866
(58) Field of Search ...................... 73/866, 53.01, 73/54.01, 54.02, 54.04, 54.08, 54.09, 54.11, 54.14; 250/339.11, 373; 356/36, 364, 365, 317, 318, 300, 301; 378/79, 80, 88

(56) References Cited

U.S. PATENT DOCUMENTS
5,417,106 * 5/1995 Grudzien, Jr. et al. ............. 73/54.14

OTHER PUBLICATIONS
G. Schramm, "A Practical Approach to Rheology and Rheometry", pp. 62–77, Haake, 1994.
R.W. Whorlow, "Rheological Techniques", Second Edition, pp. 68–81, 4 pgs. tables, Ellis Horwood, 1992.
Cinader, et al., "Mixed Orientation State Induced by Expansion Flow of A Thermotropic Liquid Crystalline Polymer", Macromolecules, vol. 31, Jul. 1998.
McHugh, et al., "Flow History—Morphology Development in Crystallizable Polymer Melts", pp. 252–257, Intern. Polymer Processing V, 1990.
McHugh, et al., "Flow–Induced Crystallization and Self-Reinforcement During Extrusion", pp. 208–211, Intern. Polymer Processing VI, 1991.
Sakellarides, et al., "Structure Formation During Polymer Blend Flows", vol. 27, pp. 1662–1674, Polym. Eng. Sci., Dec. 1987.
Bridge, et al., "On–Line Ultrasonic Monitoring of the Extrusion of $CaCO_3$–filled Polypropylen", vol. 6, pp. 219–222, J. Materials Science Letters, 1987.
Kolnaar, et al., "*In situ* X–ray Studies During Extrusion of Polyethylene", vol. 36, pp. 3969–3974, Polymer, 1995.

(List continued on next page.)

*Primary Examiner*—Robert Raevis
(74) *Attorney, Agent, or Firm*—Fish & Richardson P.C.

(57) ABSTRACT

A apparatus for studying the effects of steady and transient flow fields on a sample. The apparatus includes:

(a) a flow chamber through which a sample can flow comprising a port arranged to accommodate an analytical probe for measuring the properties of the sample as it moves through the flow chamber;

(b) a temperature-controlled thermal reservoir that houses the flow chamber;

(c) a sample reservoir comprising a chamber in communication with the flow chamber;

(d) a displacement piston arranged to apply pressure, upon activation, to a sample residing in the chamber of the sample reservoir to force the sample into the flow chamber; and (e) an actuator arranged to apply pressure to the displacement piston to activate the displacement piston.

21 Claims, 2 Drawing Sheets

OTHER PUBLICATIONS

Migler, et al., "Light–Scattering Photometer with Optical Microscope for the In–Line Study of Polymer Extrusion ", vol. 35, pp. 2935–2943, 1997.

Migler, et al. "Fluorescence Based Measurement of Temperature Profiles During Polymer Processing", vol. 38, pp. 213–221, Polymer Engineering and Science, Jan. 1998.

Ulrich, et al., "Morphology Development During Shearing of Poly(ethylene Oxide) Melts ", vol. 20, pp. 1077–1093, Journal of Applied Polymer Science, 1976.

Wu, et al., "A Rheo–Light–Scattering Instrument for the Study of the Phase Behavior of Polymer Blends Under Simple–Shear Flow", vol. 66, pp. 2914–2921, Review of Sci. Inst., Apr. 1995.

Nakatani, et al., "A Rheometer with Two–dimensional Area Detection for Light Scattering Studies of Polymer Melts and Solutions", vol. 63, pp. 3590–3598, Review of Sci. Inst., Jul. 1992.

Kim, et al., "Shear Light Scattering Photometer with Optical Microscope for the Study of Polymer Blends", vol. 67, pp. 3940–3947, Review of Sci. Inst., Nov. 1996.

Addleman, et al., "A Simple High Pressure Flow Cell for On–line Absorption, Raman, and Time Resolved Laser Induced Fluorescence Spectroscopy in Supercritical Fluids", vol.69, pp. 3127–3131, Review of Scientific Instruments, Sep. 1998.

* cited by examiner

APPARATUS FOR STUDYING THE EFFECTS OF FLOW FIELDS IMPOSED ON A MATERIAL DURING PROCESSING

CROSS REFERENCE TO RELATED APPLICATIONS

This application derives priority from a provisional application bearing Ser. No. 60/077,947 that was filed on Mar. 13, 1998 entitled "A Novel Device For Investigating The Effects of Strong Shear Fields On Crystallization of Polymers."

BACKGROUND OF THE INVENTION

This invention relates to studying the effects of flow fields imposed on a material during processing.

The engineering properties of a material are determined by the meso-, micro-, and nano-structure of the material. These features, in turn, are extremely sensitive to the processing history of the material, including the temperatures and flow fields to which the material was exposed during processing. For example, in typical commercial polymer processing operations such as extrusion molding, film blowing, or fiber spinning, a polymer melt is subjected to intense flow fields (shear, elongational, or a combination thereof), thereby distorting the melt. In the case of semi-crystalline polymers, imposing flow fields on the melt accelerates the rate of crystallization, and can result in the formation of crystallites oriented in the flow direction, both of which affect the morphology and properties of the resulting material. In the case of amorphous polymers, imposing flow fields can result in a "frozen-in" orientation that modifies the mechanical and optical properties of the material. Similarly, flow fields imposed during processing can alter the microstructure of polymer blends, filled polymers, and other materials.

Optimizing the engineering properties of materials requires an understanding of the effects of flow fields imposed during processing to permit a rational choice of suitable materials and processing conditions for a particular application. The work of Janeschitz-Kriegl et al., reported in Int. Polym. Process, 8, 236 (1993); Int. Polym. Process, 10, 243 (1995); Rheol. Acta 35, 127 (1996); and Int. Polym. Process, 12, 72 (1997), represents one approach towards understanding the underlying physics of polymer melt crystallization. Janeschitz-Kriegl subjected a subcooled polymer melt to brief, intense shearing at shear rates similar to those experienced in typical polymer processing operations by driving the polymer through a slit under high pressure generated by an extruder, after which the polymer was allowed to crystallize. The progress of crystallization was tracked using a rotating polarizer setup that monitored birefringence. The resulting data provided information regarding the relationship between crystallization time and both wall shear rate and shearing time.

The apparatus used in the Janeschitz-Kriegl studies suffers from two disadvantages that limit its commercial utility. First, using an extruder requires the use of large amounts of polymer samples, thereby limiting the number and type of polymers that can be studied. In addition, the rotating polarizer set-up limits the time resolution of the data, making it difficult to monitor the deformation of the melt during short shearing times.

Capillary rheometers have also been used to study the flow properties of polymeric materials. The rheometer is operated by forcing polymer through capillaries of varying lengths using pneumatic or hydraulic pressure, a screw feed, or a dead weight.

Capillary rheometers are typically used to study isothermal, steady state, stress-strain relationships. However, they are not well-suited for generating well-defined transient deformations and recording structure development in real time while the polymer is under the influence of the flow field.

SUMMARY OF THE INVENTION

The invention provides an improved apparatus for studying the effects of flow fields imposed during processing on the structure and properties of a material. Unlike capillary rheometers, the apparatus is well-suited for studying the effects of both steady and transient flow fields. Unlike the extruder-based device used in the Janeschitz-Kriegl studies, which required kilogram-sized samples, this apparatus is capable of establishing flow fields on the order of those encountered during typical processing operations using only small quantities of sample. For example, the apparatus is operable using samples of about 0.5 cm$^3$. Accordingly, it is well-suited for studying experimental materials that are available only in small quantities.

Another useful feature of this apparatus is that it is designed to accommodate a wide variety of real-time, in-situ probes for studying structure such as infrared, optical, and x-ray-based probes, and to facilitate subsequent ex-situ characterization by, e.g., optical or electron microscopy. For example, it is possible to use the apparatus with synchrotron x-ray sources for in-situ x-ray scattering studies of the evolution of nanostructure. Data can be acquired rapidly during the pressure pulse. For example, in some cases, data can be acquired at around 5 millisecond time resolution.

The apparatus can be used to study many different materials. It is particularly useful for studying polymer samples, including, for example, semi-crystalline polymers, amorphous polymers, engineering plastics, elastomers, thermoplastic elastomers, polymer melts, polymer blends, polymer solutions, polymer suspensions, composite structures, foams, and gels. Ceramic samples, e.g., in the form of sol-gels, can also be studied.

The apparatus includes a flow chamber through which a sample can flow. The flow chamber can be designed to accommodate various flow geometries, thereby making it possible to study a large number of different flow conditions, including uniform and non-uniform shear flow; uniaxial, biaxial, and intermediate extensional flow; and flows having both shear and extensional components. For example, the flow chamber may be provided in the form of a channel having a cross-section that remains constant along the length of the channel, or which varies along the length of the channel. In the case of channels in which the cross-section varies, the channel may be tapered or it may include abrupt contractions and/or expansions. Specific examples of suitable flow geometries include a simple rectangular channel that acts as a capillary for studying shear flow, and a channel having a tapered region for studying a mixture of shear and extensional flow. It is also possible to design the flow chamber, e.g., by incorporating obstructions in the flow chamber, in order to study flow around corners or flow around an obstacle leading to a weld line.

The flow chamber includes one or more ports arranged to accommodate one or more analytical probes for measuring the properties of the sample as it moves through the flow chamber. These ports enable data relating to the behavior of the sample to be gathered while the sample is subject to a flow field, as well as after cessation of flow.

Suitable ports include windows that are transmissive to a certain range of radiation wavelengths. One window, for example, is positioned to receive a signal from a radiation source and the other window is positioned to transmit the signal to a detector after it has passed through sample in the flow chamber. Quartz windows are useful for visible radiation, while beryllium windows are useful for x-ray radiation. Examples of other suitable windows include silicon, which is useful for infrared radiation; calcium fluoride, which is useful for visible and infrared radiation; and polyimides such as Kapton® which are useful for x-ray radiation.

The flow chamber is housed within a thermal reservoir. To facilitate ex-situ characterization of the sample after exposure to a given set of flow and thermal conditions, the flow chamber may be provided in the form, e.g., of a cartridge that can be removed from the thermal reservoir.

Because structure development (e.g., crystallization kinetics in the case of semi-crystalline polymers) can be very sensitive to temperature, the thermal reservoir is temperature-controlled, preferably to within about ±0.1° C., to ensure proper control and temperature stability. Preferably, the thermal reservoir is designed to perform transient temperature control. According to one embodiment, this objective is achieved by equipping the thermal reservoir with a pair of cartridge heaters, a thermocouple, a feedback temperature controller, and a plurality of channels extending the length of the thermal reservoir through which heat transfer fluid can be circulated. It is also desirable to equip the thermal reservoir with a transducer arranged to measure the pressure of the sample at the entrance of the flow chamber.

The apparatus further includes a sample reservoir having a chamber that opens, at one end, into the flow chamber. A sample is placed in the chamber and then heated, if desired, to a predetermined temperature to cause it to melt. To facilitate this operation, the sample reservoir is preferably temperature-controlled.

The sample is expelled under pressure into the flow chamber. The pressure is generated by a combination of a displacement piston arranged to apply pressure, upon activation, to a sample residing within the chamber of the sample reservoir, and an actuator arranged to apply pressure to the displacement piston, thereby activating it. The actuator may take many forms. For example, it may include a piston arranged to apply pressure to the displacement piston. The actuator may be driven in a number of ways, including by means of pneumatic or hydraulic sources.

The displacement piston preferably includes a shaft and a lip seal member mounted on the shaft. The seal prevents sample from leaking out of the chamber in the sample reservoir when the displacement piston acts upon the sample.

The combination of the displacement piston and actuator makes it possible to generate significant pressures on the sample, even when the sample is very small (e.g., on the order of a few cubic centimeters). For example, it is possible to apply pressures to the sample at the entrance of the flow chamber that are at least 100 times greater than the pressure acting on the displacement piston.

Other features and advantages will be apparent from the following description of the preferred embodiments thereof, and from the claims.

DETAILED DESCRIPTION

The apparatus according to the invention can be designed to accommodate a number of different flow geometries. For the sake of illustration, the apparatus is described below with reference to one particular flow geometry. However, it will be understood that different flow geometries could be used as well.

Figure 1:
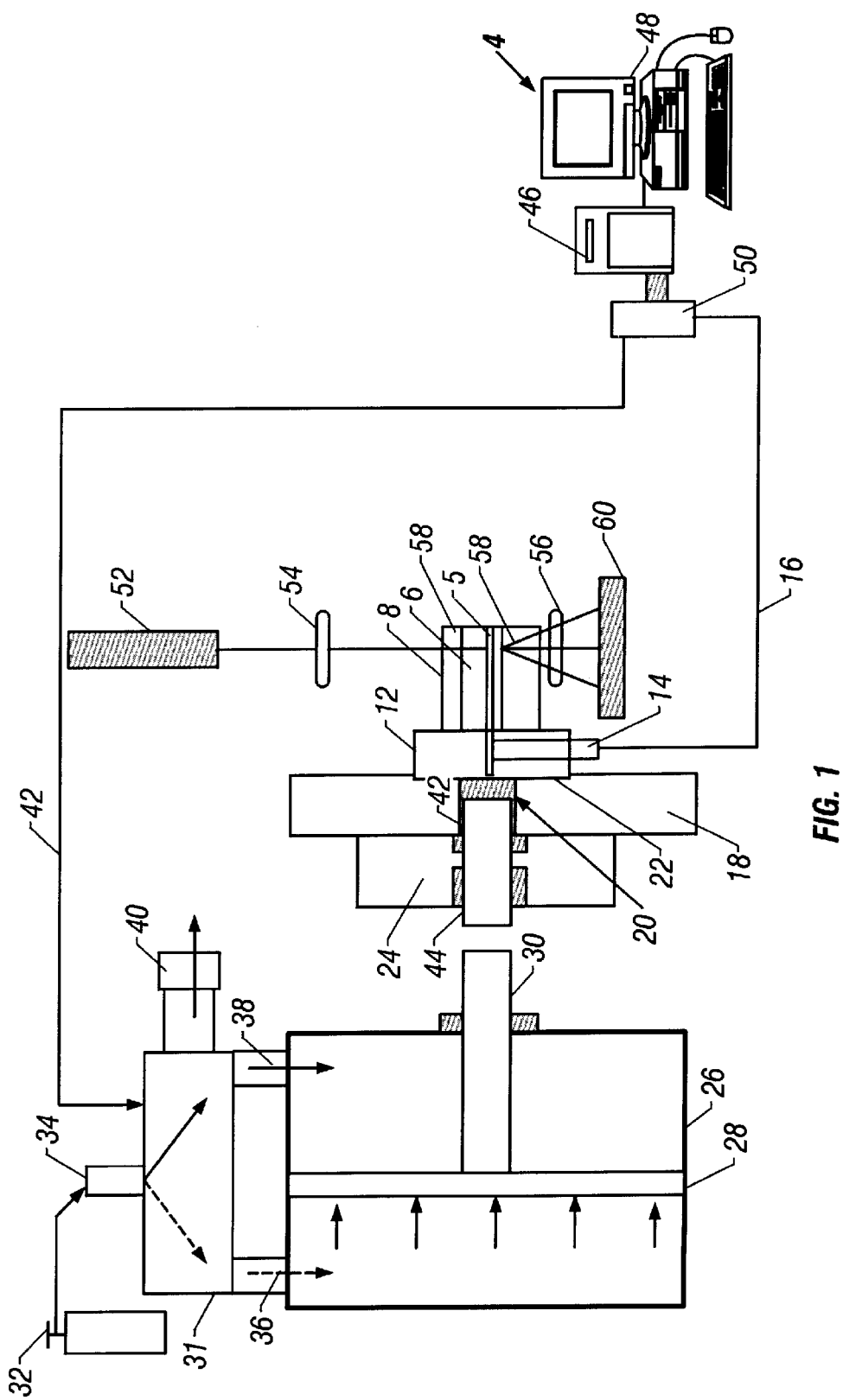
FIGS. 1 and 2 are schematic views of an apparatus according to the invention for studying the effects of steady and transient flow fields on a sample.
Figure 2:
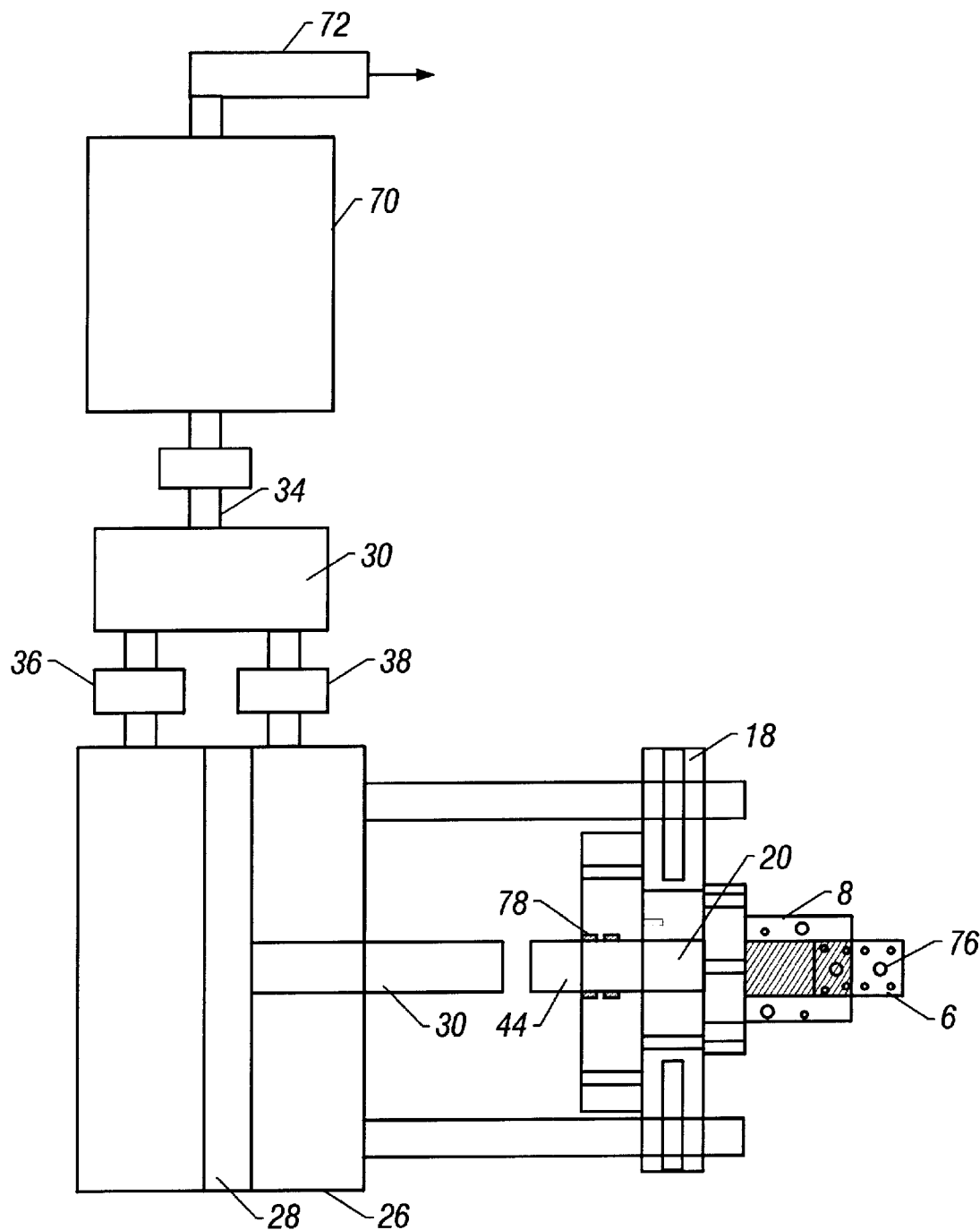

Referring to FIGS. 1 and 2, there is shown a flow apparatus 2, and a related monitoring and control station 4. Flow apparatus 2 can be used to study the behavior of materials under the influence of steady and transient flow fields, including the structure developed in the material as a result of the flow field. It is particularly useful for studying small sample sizes as low as a few cubic centimeters.

A sample is forced under pressure through a flow chamber 5 which may be formed of stainless steel or other appropriate material. Chamber 5 acts as a capillary. For shear flow experiments, chamber 5 is preferably in the form of a straight-walled slit having an aspect ratio exceeding 10. For example, chamber 5 may be in the form of a straight-walled slit having a depth of about 0.5 mm and a width of about 6.35 mm.

According to the embodiment shown in FIGS. 1 and 2, flow chamber 5 is provided as part of a flow cartridge 6 that is removably housed in a heating block 8 that acts as a thermal reservoir for flow chamber 5. Block 8 may be formed of brass or another appropriate heat conductive material. Flow cartridge 6 is held in place by a restraining plate (not shown) that is bolted onto block 8. The restraining plate may be constructed from stainless steel or other appropriate material.

Block 8 is constructed such that it provides even heating to flow chamber 5. To accomplish heating, block 8 includes a pair of symmetrically mounted cartridge heaters 12 inserted into block 8. The temperature of block 8 is monitored by a heat sensor such as a stainless steel sheathed J-type thermocouple (not shown) embedded in block 8. The heat sensor is operably linked to a feedback PID temperature controller such as a controller made by Omega Engineering Inc., Stamford, Conn., and monitoring and control station 4. This arrangement continually monitors the temperature within block 8 and makes adjustments where appropriate in order to maintain the desired temperature.

Temperature stability in heating block 8 is enhanced by providing channels cut through the length of block 8 to circulate heat transfer oil such as Fluid CTB from Paratherm Co., Conshohoken, Pa. A high temperature recirculating bath such as a Model TP-12 from Julabo, USA, Kutztown, Pa. is used to pump the oil through the channels. Temperature control and stability to within ±0.5° C., and preferably to within ±0.1° C., can be achieved.

Block 8 can be provided with a pressure transducer 14 to measure the pressure of the sample as it flows into flow chamber 5. Pressure transducer 14 is mounted flush to flow chamber 5. A representative pressure transducer is sold by Dynisco Measurement/Control, Sharon, Mass., and has a range of up to 10,000 psi. Signals from pressure transducer 14 are transmitted through line 16 to monitoring and control station 4.

Block 8 is bolted to an aluminum block 18 that includes a chamber 20 for holding a sample. Chamber 20 is heated by four cartridge heaters (not shown) provided with independent feedback PID control to heat the sample. Chamber 20 is thermally isolated from block 8 by a gasket 22 (preferably is a ⅛-inch mica gasket). In addition, chamber 20 is clad with thermal insulation, such as flexible fiberglass insulation, to maintain a constant temperature in chamber 20.

A back plate 24 is provided on the back edge of block 18. Back plate 24 includes a central passage through which a displacement piston 44 extends. The distal end of displacement piston 44, which may be formed as a 1 inch stainless steel rod, serves as the back edge of chamber 20. A brass-ring bearing 78 disposed around the circumference of displacement piston 44 holds piston 44 in place.

Displacement piston 44 includes a peripheral lipseal, for example from All Seals Inc., Santa Ana, Calif., to prevent leakage from chamber 20. The material for the seal is selected from materials that are capable of withstanding the temperatures and pressures encountered during a typical flow experiment.

To prevent wear on the seal when displacement piston 44 is inserted in back plate 24, displacement piston 44 is provided with a slight taper at its distal end. Displacement piston 44 is driven forward under high levels of force to push sample from chamber 20 through flow chamber 5 under high pressures, thereby setting up a flow field that acts on the sample as it flows through flow chamber 5. As shown in FIGS. 1 and 2, the driving force is generated by a pneumatically driven actuator 26, e.g., of the type sold by Hydroline Inc., Rockford, Ill. However, other types of actuating means such as hydraulic means may be used as well. Actuator 26 preferably includes a shaft 30 that contacts the end of displacement piston 44 to drive displacement piston 44 forward into chamber 20. Shaft 30 is attached to an actuator plate 28 residing inside actuator 26. Pneumatic pressure on one side of actuator plate 28, such as pressure from compressed nitrogen gas, drives shaft 30 in one direction, while higher pressure on the other side of actuator plate 28 drives shaft 30 in the opposite direction.

Pressure is provided to actuator 26 by means of a valve 31 through connectors 36, 38. Valve 31 also controls the pressure of the fluid or gas delivered from a pressure source such as nitrogen source 32. A fitting 34 is attached to valve 31. Valve 31 preferably is a fast-switching solenoid-activated valve, such as that produced by Ross Operating Valve Co., Troy, Miss. To provide for faster switching of valve 31, gas from valve 31 is preferably routed to a surge tank 70 mounted on valve 31. Pressure line 72 leads from a gas pressure source to surge tank 70.

Valve 31 is controlled by monitoring and control station 4 through signal line 42. Valve 31 also includes an exhaust port 40, which permits release of pressurized fluid or gas from actuator 26.

Flow apparatus 2 is ported to one or more instruments to measure the properties of the sample in-situ. To accomplish this, block 8 and flow chamber 5 (through flow cartridge 6) are provided with observation ports 58 and 58' located near the distal end of block 8 and flow cartridge 6, where pressures are close to atmospheric pressure. Observation ports 58 and 58' may be provided with windows, such as ⅛-inch thick quartz windows for optical measurements or ½ mm beryllium windows for x-ray measurements. The windows are mounted using a high temperature epoxy adhesive. A radiation source 52 is positioned to generate a signal that may through focussing optics 54 before entering incident observation port 58, passing through sample within flow chamber 5, and leaving through outgoing observation port 58'. The outcoming signal may then pass through another set of focussing optics 56 to a sensor 60 where the signal is detected and processed to obtain information regarding the properties of the sample.

The ports are shown in greater detail in FIG. 2. As shown in FIG. 2, flow cartridge 6 includes an incident port 76 to permit monitoring of sample within flow chamber 5, for example, by passing radiation through incident port 76. Incident port 76 may have either parallel or tapered sides. The corresponding port in block 8 can also have a cylindrical or conical aperture to enable light scattering measurements to be performed.

According to one useful detection set-up, optical measurements are made using a 632.8 nm He—Ne laser as a radiation source. Radiation from the laser is polarized at 45° to the polymer flow direction and then passed through the sample in flow chamber 5. After exiting the sample, the radiation then impinges upon a polarizing beam-splitting prism, such as those produced by Newport Co., Irvine, Calif., having an alignment perpendicular to that of the original polarization state of the radiation. A pair of photo-detector diodes, such as those produced by Thor Labs Inc., Newton, N.J., then receives the radiation and measures its intensity, both in the plane parallel to (Ipar) and the plane perpendicular to (Iperp) the initial polarization state. The birefringence, $\Delta n$, is then calculated from the values of Ipar and Ipe. The birefringence provides an estimate of the extent of anisotropy in the material.

For systems with structure developing on a micrometer scale, turbidity measurements can provide an estimate of the extent of structure development. For example, in the case of semi-crystalline polymers, turbidity provides an estimate of the extent of crystallization.

Other useful instruments for monitoring the evolution of structure in the material as it develops both at the micron scale and the nanometer scale include real-time, in-situ small angle light scattering (SALS), which provides micron-scale information about the evolution of crystalline order; small angle x-ray scattering (SAXS), using synchrotron radiation, which provides information at the nanometer level; and wide angle x-ray diffraction (WAXD), which can be used to determine unit cell parameters in ordered materials. In addition, different types of elastic and inelastic spectroscopy, including light scattering and Raman scattering, can be incorporated, as can microscopes using light or fluorescent probes.

Flow apparatus 2 can also be used in connection with methods such as infrared dichroism for probing the behavior of selectively labelled species in the sample. Polarization modulation techniques can be used to increase the sensitivity of dichroism detection.

The operation of flow apparatus 2 is controlled by monitoring and control station 4. Monitoring and control station 4 includes an input/output terminal 48 operably connected to a computer 46. Computer 46 may monitor and control flow apparatus 2 directly, or it may be equipped with a data acquisition expansion board, such as an NB-MIO-16X from National Instruments, Austin, Tex. Computer 46 is operated with software to retrieve and analyze data, and is preferably configured to acquire data with a resolution of 5 ms so that distortion of the sample as it is exposed to the flow field may be studied in real time.

The invention will now be described further by way of the following non-limiting examples.

EXAMPLES

Flow apparatus 2 was used to study the melt behavior of a semicrystalline isotactic polypropylene sample (melt index=12, nominal melting temperature=165° C.) in a pair of experiments.

Example 1

The polypropylene sample was placed in chamber 20 and heated at 200° C., which is well above the nominal melting point of the polymer (165° C.), to melt the sample. Heating block 8 was likewise maintained at 200° C. Following melting, the sample was caused to flow into flow chamber 5 under a pressure (measured across the entrance to flow chamber 5 using a transducer) of 2000 psi (corresponding to a wall shear stress of around 0.04 MPa). As the melt flowed through flow chamber 5, its birefringence was measured in real time using a crossed polarizer set-up and laser light as the radiation source ported directly to flow cartridge 6, as described above. The results of the experiment provided information regarding the nonlinear rheology of the polymer melt on inception of shear flow, and its relaxation after cessation of flow.

Example 2

The experimental set-up used in Example 2 was the same as the experimental set-up used in Example 1. The polypropylene sample was placed in chamber 20 and heated at 200° C., again well above the nominal melting point of the polymer (165° C.), to melt the sample. Heating block 8 and flow chamber 5 were maintained at 163° C. Following melting, the sample was caused to flow into flow chamber 5 at low pressure (c.a. 500 psi), and then allowed to equilibrate for 5 minutes to create a subcooled polymer.

At the end of the equilibration period, a pressure of around 2600 psi was applied to the subcooled polymer sample for four seconds. Measurements of laser intensity transmitted through the sample provided information regarding the effect of the flow field on crystallization kinetics. In addition, analysis of polarized light passed through the polymer sample provided information regarding the extent to which crystallites formed under the influence of the flow field were oriented.

Other embodiments are within the following claims.

What is claimed is:

1. An apparatus for studying the effects of steady and transient flow fields on a sample,
   said apparatus comprising:
   (a) a flow chamber through which a sample can flow comprising a port arranged to accommodate an analytical probe for measuring the properties of the sample as it moves through said flow chamber;
   (b) a temperature-controlled thermal reservoir that houses said flow chamber;
   (c) a sample reservoir comprising a chamber in communication with said flow chamber;
   (d) a displacement piston arranged to apply pressure, upon activation, to a sample residing in said chamber of said sample reservoir to force the sample into said flow chamber; and
   (e) an actuator arranged to apply pressure to said displacement piston to active said displacement piston,
   wherein said apparatus is capable of rapidly and controllably altering the flow fields to which the sample is exposed.

2. An apparatus according to claim 1 wherein said flow chamber is removably housed within said thermal reservoir.

3. An apparatus according to claim 1 wherein said sample reservoir is temperature-controlled.

4. An apparatus according to claim 1 wherein said temperature-controlled thermal reservoir is capable of performing transient temperature control.

5. An apparatus according to claim 1 wherein said actuator comprises a piston arranged to apply pressure to said displacement piston to activate said displacement piston.

6. An apparatus according to claim 1 wherein said actuator comprises a pneumatically driven actuator.

7. An apparatus according to claim 1 wherein said actuator comprises a hydraulically driven actuator.

8. An apparatus according to claim 1 wherein said flow chamber comprises a plurality of ports arranged to accommodate an analytical probe for measuring the properties of a sample as it moves through said flow chamber.

9. An apparatus according to claim 8 wherein said ports comprise a pair of windows mounted in said flow chamber.

10. An apparatus according to claim 9 wherein said windows comprise quartz windows.

11. An apparatus according to claim 9 wherein said windows comprise beryllium windows.

12. An apparatus according to claim 9 wherein said windows comprise silicon windows.

13. An apparatus according to claim 9 wherein said windows comprise calcium fluoride windows.

14. An apparatus according to claim 9 wherein said windows comprise polyimide windows.

15. An apparatus according to claim 1 wherein said displacement piston comprises a shaft and a lip seal member mounted on said shaft.

16. An apparatus according to claim 1 wherein said temperature-controlled thermal reservoir comprises a transducer arranged to measure the pressure of a sample at the entrance of said flow chamber.

17. An apparatus according to claim 1 wherein said displacement piston and said actuator together are capable of applying a pressure to a sample at the entrance of said flow chamber that is at least 100 times greater than the pressure applied to said displacement piston.

18. An apparatus according to claim 1 wherein said temperature-controlled thermal reservoir comprises:
   (a) a pair of cartridge heaters;
   (b) a thermocouple;
   (c) a feedback temperature controller; and
   (d) a plurality of channels through which heat transfer fluid can be circulated.

19. An apparatus according to claim 1 wherein said actuator comprises a three-way valve.

20. An apparatus according to claim 1 wherein said flow chamber comprises a flow channel.

21. An apparatus according to claim 20 wherein said flow channel has a cross-section that varies along the length of said channel.

* * * * *